Figure 1A:
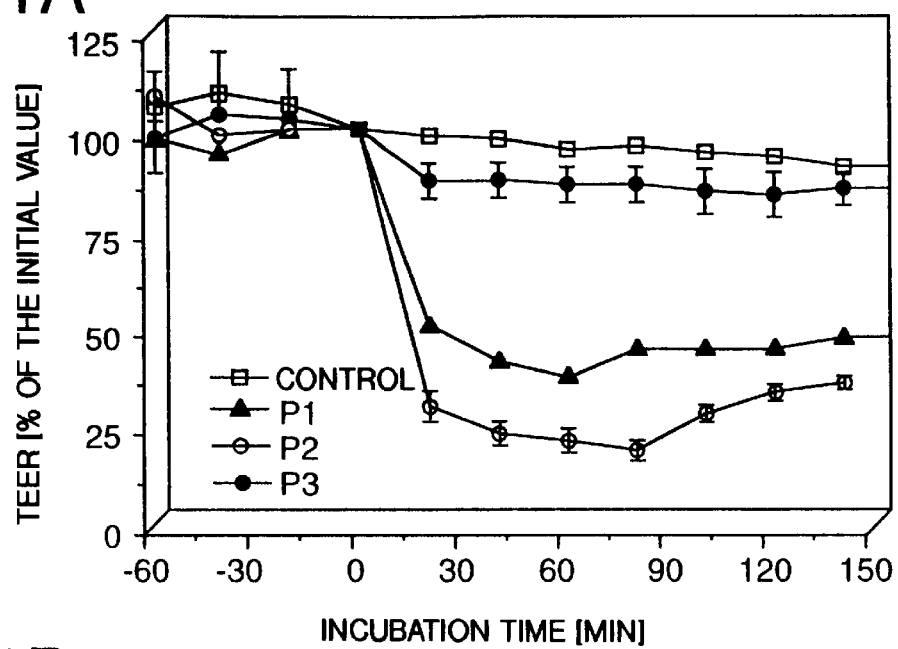

United States Patent [19]

Luessen et al.

[11] Patent Number: 6,004,575
[45] Date of Patent: Dec. 21, 1999

[54] USE OF (METH) ACRYLIC ACID/MALEIC ACID COPOLYMERS FOR IMPROVING MUCOSAL PERMEABILITY

[75] Inventors: Henrik L. Luessen, Rengsdorf; Gerrit Borchard, Saarbrücken; Albertus G. de Boer, Oegstgeest; Hans E. Junginger, Rijnsburg; Karl Kolter, Limburgerhof; Volker Schehlmann, Römerberg; Axel Sanner, Frankenthal, all of Germany

[73] Assignee: BASF Aktiengesellschaft, Ludwigshafen, Germany

[21] Appl. No.: 08/902,938

[22] Filed: Jul. 30, 1997

[51] Int. Cl.⁶ .............................. A61K 47/32; A61K 9/22
[52] U.S. Cl. .................. 424/434; 514/772.6; 424/435; 424/436; 424/437; 424/427
[58] Field of Search ............................................. 424/434

[56] References Cited

U.S. PATENT DOCUMENTS

| | | | |
|---|---|---|---|
| 4,615,697 | 10/1986 | Robinson | 604/890 |
| 4,876,092 | 10/1989 | Mizobuchi et al. | 424/434 |
| 5,364,634 | 11/1994 | Lew | 424/434 |
| 5,672,356 | 9/1997 | Rault et al. | 424/434 |
| 5,714,165 | 2/1998 | Repka et al. | 424/486 |

FOREIGN PATENT DOCUMENTS 9308863  12/1997  Japan.

*Primary Examiner*—Peter F. Kulkosky
*Attorney, Agent, or Firm*—Keil & Weinkauf

[57] ABSTRACT

(Meth)acrylic acid/maleic acid copolymers for improving mucosal permeability and pharmaceutical compositions containing them are described.

9 Claims, 3 Drawing Sheets

USE OF (METH) ACRYLIC ACID/MALEIC ACID COPOLYMERS FOR IMPROVING MUCOSAL PERMEABILITY

DESCRIPTION

The present invention relates to the use of (meth)acrylic acid/maleic acid copolymers for improving mucosal permeability.

Epithelial tissue forms an important permeation barrier to the paracellular transport of hydrophilic active ingredients, especially those of high molecular weights. What are called "tight junctions" (intercellular junctions between adjacent epithelial cells where the plasma membranes are in direct contact) ensure that the internal environment of an organ is sealed off from the external one. The passive paracellular permeability of these epithelial cells is determined by the tightness of the intercellular contact points. Widening of the "tight junctions" leads to improved absorption and thus to a higher bioavailability of active ingredients.

Hence there has been no lack of attempts in the past to develop methods for opening intercellular contact points. It has emerged from this that the use of both surface-active ingredients and of $Ca^{2+}$-chelating substances were promising approaches.

However, J. Controlled Rel., 29 (1994) 253 states that on use of surface-active substances there is a risk of cytolysis and, associated with this, toxic side effects.

Numerous publications, inter alia in J. Controlled Rel., 36 (1995) 25; Chem. Pharm. Bull. 33 (1985) 4600; The Journal of Cell Biology, 87 (1980) 736 and Int. J. Pharm., 90 (1993) 229 describe the effect of EDTA or EGTA on the permeability of various cell systems, eg. of Caco-2 cells. According to these, the presence of $Ca^{2+}$-chelating substances may lead to rapid, but frequently irreversible, opening of the tight junctions. In addition, in the case of EDTA, relatively high concentrations are required for an effect to be observed (reduction in transepithelial resistance) at neutral pH. In addition, complexing agents with a molecular weight $\leq 20$ kDa are associated with the risk that they undergo systemic absorption and thus may result in unwanted toxic side effects.

It was possible to show, in J. Controlled Rel., 29 (1994) 329, that nonabsorbable high molecular weight compounds based on crosslinked polyacrylates such as polycarbophil (Noveon® AA1, B. F. Goodrich) are likewise able to open tight junctions. There are technical disadvantages on use thereof because of their extremely high molecular weight (>1.000 kDa) and their high viscosity even at low concentrations ($\geq 0.5\%$ by weight).

It is furthermore known that polymers with bioadhesive properties are able to improve the bioavailability of active substances. Thus, for example, EP-A-587 047 describes the use of copolymers of (meth)acrylates with various carboxylic acids for gestagen-based pharmaceutical compositions.

EP-B-410 422 discloses the possibility of increasing the bioavailability of active substances of low solubility by them being after formulation, owing to the effect of (meth)acrylic acid/(meth)acrylate copolymers, amorphous and thus more soluble.

It is an object of the present invention to find polymers with chelating properties which increase the permeability of epithelial cells without at the same time having the above-mentioned technical disadvantages on use or causing toxicity problems.

We have found that this object is achieved by using (meth)acrylic acid/maleic acid copolymers, in particular those comprising a) 10–90 mol % of (meth)acrylic acid, b) 90–10 mol % of maleic acid and c) 0–40 mol % of other monomers to improve mucosal permeability.

The initial monomers a) are acrylic acid and/or methacrylic acid, their anhydrides, their salts or mixtures of the two carboxylic acids, anhydrides and salts mentioned. Monomer b) can be maleic acid, its salt or maleic anhydride.

Monomers a) and b) may also be incorporated partly in the form of their salts. This can be achieved, for example, by adding a base before, during or after the polymerization. If the monomers are in the form of their salts, then the alkaline earth metal, alkali metal or ammonium salts or the salts of organic amines are preferred, and the alkali metal or ammonium salts are particularly preferred.

Monomers of group c) are vinylsulfonic acid and/or hydroxy-$C_2$–$C_6$-alkyl esters of acrylic or methacrylic acid and/or acrylic or methacrylic esters of saturated, linear or branched $C_1$–$C_{40}$-alcohols. Examples are methyl, ethyl, n-propyl, i-propyl, n-butyl, i-butyl, tert-butyl, n-hexyl, n-octyl, i-nonyl, n-decyl, n-dodecyl, n-tetradecyl, n-hexadecyl, n-heptadecyl, n-octadecyl, n-nonadecyl, n-eicosyl, n-docosyl, n-tetracosyl, 2-ethylhexyl, i-bornyl acrylate or cyclohexyl acrylate or the corresponding methacrylates. $C_1$-, $C_2$- and/or $C_6$–$C_{30}$-alkyl acrylates or methacrylates are preferably employed. $C_8$–$C_{22}$-Alkyl acrylates or methacrylates are particuliarly preferably employed.

The hydroxyalkyl groups in monomers c) are derived, for example, from alkanediols such as 1,2-ethanediol, 1,3- and 1,2-propanediol and technical mixtures thereof, 1,4-, 1,3- and 2,3-butanediol and their mixtures. Examples which may be mentioned are hydroxyethyl acrylate, hydroxyethyl methacrylate, hydroxypropyl acrylates, hydroxypropyl methacrylates, hydroxybutyl acrylates, hydroxybutyl methacrylates. Preferred hydroxyalkyl esters c) are hydroxyethyl acrylate, hydroxypropyl acrylates and hydroxybutyl acrylates. Particularly preferred hydroxyalkyl esters c) are the hydroxypropyl acrylates, and those of particular industrial importance are the isomeric mixtures of 2-hydroxy-1-propyl acrylate and 1-hydroxy-2-propyl acrylate prepared by reacting acrylic acid with propylene oxide.

The (meth)acrylic acid:maleic acid molar ratio in the copolymer to be used according to the invention can be varied widely. It is, for example, in the range from 90:10 to 10:90, preferably fromn 70:30 to 30:70. When monomer c) is present, an advantageous monomer distribution is in the range from 5 to 40, in particular 10 to 35, mol % of c) and 95 to 60 mol % of a) and b), in which case the ratios of a) and b) can be chosen as mentioned above.

The copolymers are prepared in a conventional way by suspension polymerization, precipitation polymerization or solution polymerization, with solution polymerization in aqueous solution being a preferred method. Examples of such polymers are given in EP-A-0 168 547, EP-A-0 075 820 or EP-A-0 349 810. This results in copolymers with a weight average molecular weight of from 500 to 1 million. Particularly suitable for the use according to the invention are copolymers with a molecular weight of from 5000 to 500,000, in particular 10,000 to 300,000.

The copolymers of a) and b), with or without c), are normally administered in the form of pharmaceutical compositions together with the active substance. Suitable pharmaceutical forms are tablets, extrudates, granules, pellets, powders, capsules, suppositories, ointments, solutions, suspensions or emulsions, and administration can take place, depending on the application, orally, sublingually, buccally, rectally, through the lungs, nasally or through the mucosa of the eyes. The content of copolymer to be used according to the invention in these pharmaceutical forms is generally greater than 10% by weight, preferably greater than 30, particularly preferably greater than 50, % of the total weight of the pharmaceutical form. However, it is also possible first to treat the mucosa, eg. of the stomach, intestine, nose, mouth, throat or eye, with the permeability-increasing copolymer and then to administer the pharmaceutical active substance.

The abovementioned pharmaceutical compositions are, as a rule, produced with the addition of bulking agents, binders, disintegrants, lubricants or other ancillary substances. Used as bulking agents and dry binders for tablets are, inter alia, lactose, sucrose, mannitol, sorbitol, microcrystalline cellulose, starch, dicalcium phosphate and polyglycols. Binders suitable for granulation are starch, alginates, polyvinylpyrrolidone and, in particular, carboxymethylcellulose. Examples of suitable lubricants are starch, talc and silicon dioxide. Lubricants which can be used for mechanical production of tablets are magnesium stearate and metal soaps. Tablet disintegrants which can be used include starch, cellulose derivatives, alginates, dextrans and crosslinked polyvinylpyrrolidone.

Depending on the application and active substance, the copolymers are advantageously used in neutralized, partly neutralized or unneutralized form. If the copolymers are in unneutralized form, it is often advantageous for a base or a proton acceptor, consisting either of another ancillary substance and/or directly of the active substance, to be present.

If the active substance is basic it can be wholly or partly in salt form with the copolymer of a) and b), with or without c), according to the invention.

The following Examples illustrate the use, according to the invention, of the (meth)acrylic acid:maleic acid copolymers, with their permeability-increasing effect being demonstrated in an in vitro test system using human intestinal epithelial cells (caco-2 cell cultures) as example. Caco-2 cells have many differentiation properties of epithelial cells such as asymmetric distribution of enzymes, morphologically similar structure with microvilli on the apical side of the cells and formation of a monolayer with tight junctions. Cultivation of these cells on porous membranes in what are called transwell plates makes it possible to investigate accurately transport from the apical compartment (intestinal lumen) into the basolateral compartment (lymph). In this, the extent to which the tight junctions are opened or closed are shown both by the transepithelial electrical resistance (TEER) and by the permeation of radioactive tracers ($^{14}$C-mannitol) through the cell monolayer. A reversible improvement in permeability can be identified from measurements of the TEER by a renewed rise in resistance after replacement of the apical test medium by the original apical medium.

EXPERIMENTAL EXAMPLES

1. Determination of the transepithelial resistance (TEER):

Caco-2 cells cultivated on polycarbonate filters (diameter 6.5 mm) were further cultured in Costar transwell chambers (Costar Europe Ltd., Badhoevedorp, NL) to a cell density of $10^4$ cells/cm$^2$. The culture medium used in both half-cells was DMEM (Dulbecco's Modified Eagle's Medium, Sigma) with the addition of 1% of a nonessential amino acid solution, 10% fetal bovine serum, benzyl-penicillin G (160 U/ml) and streptomycin sulfate (100 μg/ml), replacing the medium each day. The culture plates were incubated at 37° C. in an atmosphere of 95% air and 5% $CO_2$.

The polymers to be investigated (see Table 1) were dissolved in various concentrations (1–7.5%) in DMEM and neutralized with NaOH. Control experiments were carried out in DMEM. The transepithelial resistance (TEER) of the individual filters was measured after incubation at intervals of 20 minutes using a Millicell Electrical Resistance System supplied by Millipore B. V.(Etten-Leur, NL). To check the reversibility of the cell-cell interaction, after 2 h the polymer solution was replaced by pure DMEM and the resistance was measured again.

TABLE 1

Structure of the polymers investigated

| Polymer | Structure | average molecular weight |
|---|---|---|
| 1 | AA/MA = 70/30 | 70000 |
| 2 | AA/MA = 70/30 | 150000 |
| 3 (comparison) | AA = 100 | 250000 |
| 4 | AA/MA/HPA = 40/40/20 | 20000 |
| 5 | AA/MA = 50/50 | 50000 |
| 6 | AA/MA/VAS = 35/35/30 | 15000 |

Figure 1B:
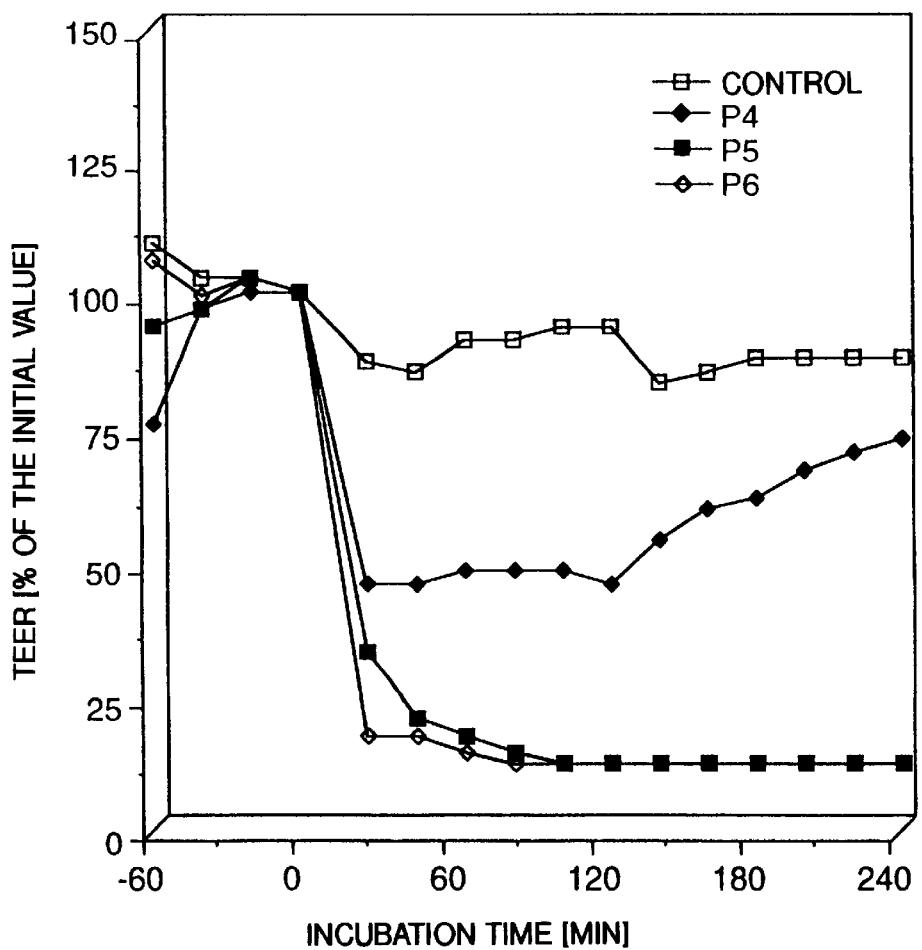

Abbreviations:
AA: acrylic acid
MA: maleic acid
HPA: hydroxypropyl acrylate
VAS: vinylsulfonic acid FIG. 1 A/B shows the results of the experiments with polymers 1 to 6 (5% strength solution in DMEM). It is evident that the transepithelial electrical resistance falls markedly on use of copolymer 1, 2 and 4 to 6, whereas only a slight reduction is observed with comparison polymer 3.

Figure 2:
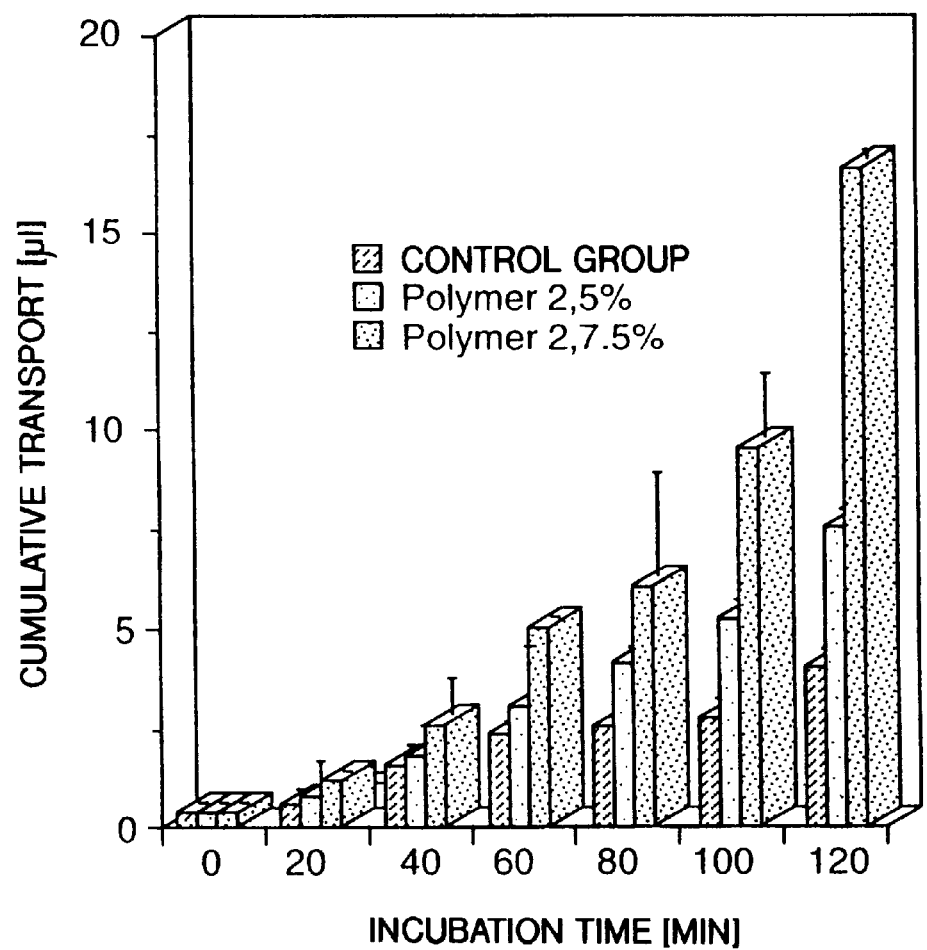
Figure 3:
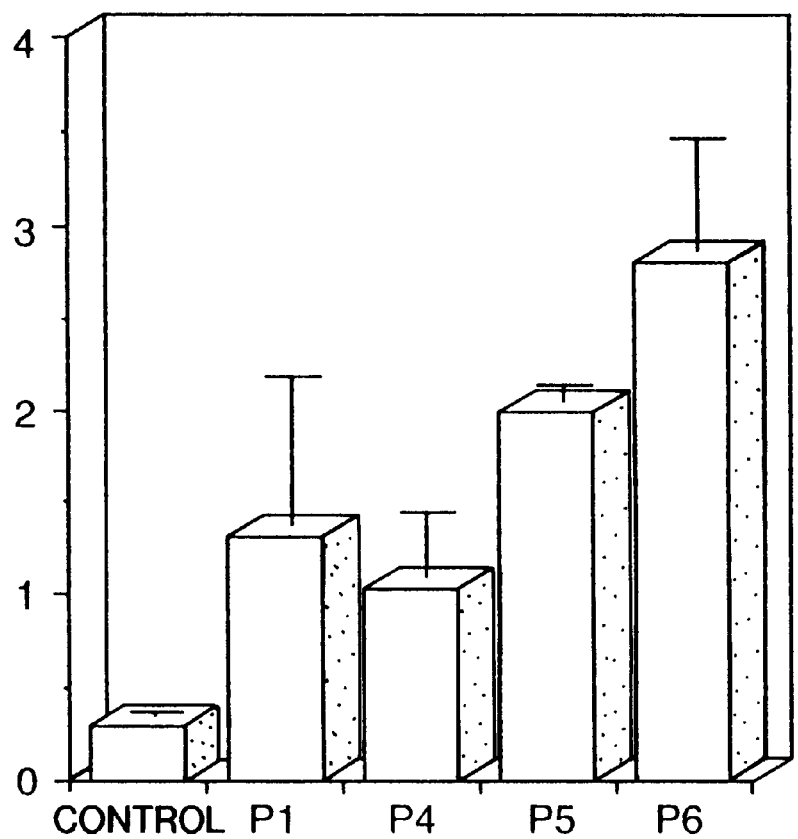

2. Determination of $^{14}$C-mannitol penetration:

The increase in paracellular transport was investigated by incubating the cellular monolayer with a suitable hydrophilic tracer ($^{14}$C-mannitol, 4 μmol/l, specific activity: 0.2 μCi/ml) in the presence of a 5 or 7.5% strength polymer solution. In each case after 30 minutes, 200 μl samples were taken from the acceptor chamber and their radioactivity was checked (Tri-carb 1500 scintillation counter, Packard Instr. B. V., Groningen, NL). As FIGS. 2 (5 and 7.5% strength solution of polymer 2 in DMEM) and 3 (5% strength solution of polymers 1, 4–6 in DMEM, incubation time 120 min) show, incubation of caco-2 cells in the presence of investigated copolymers 1, 2 and 4 to 6 leads to an opening of the tight junctions between the epithelial cells and, by comparison with the control, to a significant increase in the rate of transport of the radioactive tracer.

3. Examples of pharmaceutical forms.

| a. Atenolol tablets | |
|---|---|
| Atenolol | 50 mg |
| Ludipress ® | 50 mg |
| Acrylic acid/maleic acid copolymer (50:50) sodium salt (molecular weight 50000) | 146.5 mg |
| Aerosil ® 200 | 2 mg |
| Kollidon ® VA64 | 1 mg |
| Magnesium stearate | 1.5 mg |
| Tablet weight | 260 mg |

1000 g of atenolol, 1000 g of Ludipress® (BASF), 2930 g of acrylic acid/maleic acid copolymer (50:50) sodium salt, 40 g of Aerosil® 200 (Degussa), 200 g of Kollidon® VA64 (BASF) and 30 g of magnesium stearate were initially screened through a 0.8 mm screen and mixed in a Turbula mixer for 5 min. Biconvex tablets with a diameter of 9 mm were then produced in a rotary tablet press with a pressure of 22 kN.

| b. Sulfasalazine film-coated tablets | |
| --- | --- |
| Sulfasalazine | 250 mg |
| Acrylic acid/maleic acid copolymer (70:30) sodium salt (molecular weight 70000) | 500 mg |
| Kollidn ® 30 | 15 mg |
| Aerosil ® 200 | 2 mg |
| Magnesium stearate | 3 mg |
| Tablet weight | 770 mg |

500 g of sulfasalazine and 1000 g of acrylic acid/maleic acid copolymer (70:30) sodium salt were mixed in a Stephan mixer for 2 min and, while stirring, a solution of 30 g of Kollidon® 30 in 230 g of isopropanol was added. The moist composition was passed through a screen with a mesh width of 1.0 mm and dried on a tray at room temperature. After the dry material had been screened through a 1.0 mm screen, 4.0 g of Aerosil 200 and 6.0 g of magnesium stearate were added and mixed for 5 min. The powder mixture was then compressed to football-shaped tablets with dimensions 19×8.5 mm in a rotary press under a pressure of 35 kN and a speed of 30 rpm.

In a 2nd step, the tablets were provided with an enteric film coating in a horizontal drum coater. The spray dispersion for application with inlet air at 50° C. had the following composition:

| | |
| --- | --- |
| Titanium dioxide | 0.5% |
| Talc | 2% |
| Sicovit ® Rot 30 | 0.5% |
| Kollidon ® 30 | 0.5% |
| Methacrylic acid/ethyl acrylate copolymer (1:1) | 15% |
| Triethyl citrate | 1.5% |
| Water | 80% |

100 mg of this dispersion, corresponding to 15 mg of methacrylic acid/ethyl acrylate copolymer, were applied per tablet.

| c. Furosemide microtablets | |
| --- | --- |
| Furosemide | 1 mg |
| Acrylic acid/maleic acid copolymer (70:30) sodium salt | 5.7 mg |
| Kollidon ® VA64 | 0.2 mg |
| Aerosil ® 200 | 0.05 mg |
| Magnesium stearate | 0.05 mg |
| Tablet weight | 7.0 mg |

100 g of furosemide, 570 g of acrylic acid/maleic acid copolymer (70:30) sodium salt and 20 g of Kollidon® VA64 were mixed in a Stephan mixer and, while stirring, moistened with 105 g of isopropanol. The moist composition was forced through a screen with a mesh width of 0.6 mm, and was dried in a thin layer on a tray at room temperature for 24 h. The dry granules were passed through a 0.8 mm screen, mixed with magnesium stearate and Aerosil® 200 which had likewise been screened and mixed in a Turbula mixer for 5 min, and again passed through a 0.8 mm screen. Then, biconvex microtablets with a diameter of 2 mm and a height of about 2 mm were produced in a Korsch EKO eccentric press. For a dose of 40 mg per separate form, two-piece gelatin capsules were packed with 40 microtablets in each case.

| d. Methyldopa tablets | |
| --- | --- |
| Methyldopa | 250 mg |
| Acrylic acid/maleic acid copolymer (50:50) sodium salt (molecular weight 50000) | 347.5 mg |
| Aerosil ® 200 | 3.5 mg |
| Kollidon ® VA64 | 26 mg |
| Magnesium stearate | 3 mg |
| Tablet weight | 630 mg |

2500 g of methyldopa, 3475 g of acrylic acid/maleic acid copolymer (50:50) sodium salt, 35 g of Aerosil 200, 260 g of Kollidon® VA64 and 30 g of magnesium stearate were initially screened through a 0.8 mm screen and mixed in a Turbula mixer for 5 min. This powder mixture was then compressed to biplanar, bevelled tablets with a diameter of 12 mm in a rotary tablet press under a pressure of 30 kN and at a rate of 30 revolutions per min.

| e. S-Adenosylmethionine pastilles | |
| --- | --- |
| S-Adenosylmethionine | 100 mg |
| Acrylic acid/maleic acid copolymer (50:50) sodium salt | 700 mg |
| Mannitol | 200 mg |
| Aspartame | 3 mg |
| Orange flavor | 5 mg |
| Kollidon ® VA 64 | 82 mg |
| Aerodil ® 200 | 5 mg |
| Magnesium stearate | 5 mg |
| Pastille weight | 1100 mg |

500 g of S-adenosylmethionine, 3500 g of acrylic acid/maleic acid copolymer (50:50) sodium salt, 1000 g of mannitol, 15 g of aspartame, 25 g of orange flavor and 410 g of Kollidon® VA 64 were initially screened through a 0.8 mm screen and mixed in a Turbula mixer for 5 min. Then 25 g of magnesium stearate and 25 g of Aerosil® 200, which had previously been screened through a 0.5 mm screen, were added and mixed in for 2.5 min. Biplanar, bevelled tablets weighing 1100 mg were produced in a rotary tablet press under a pressure of 35 kN and at a rate of 30 rpm.

| f. Cefuroxime granules | |
| --- | --- |
| Cefuroxime axetil (equivalent to 250 mg of cefuroxime) | 300.7 mg |
| Acrylic acid/maleic acid copolymer (50:50) sodium salt (molecular weight 50000) | 1000 mg |
| Methacrylic acid/methyl methacrylate copolymer (1:1) | 150 mg |
| Sucrose | 502.3 mg |
| Orange flavor | 5 mg |
| Aspartame | 2 mg |
| Kollidon ® VA 64 | 40 mg |
| Granule weight | 2000 mg |

300.7 g of cefuroxime axetil (equivalent to 250 g of cefuroxime), 1000 g of acrylic acid/maleic acid copolymer (50:50) sodium salt, 150 g of methacrylic acid/methyl methacrylate copolymer (1:1), 502.3 g of sucrose, 5 g of orange flavor and 2 g of aspartame were mixed in a Stephan mixer and, while stirring, moistened with a solution of 40 g of Kollidon® VA 64 in 310 g of isopropanol. The moist composition was forced through a screen with a mesh width of 1.2 mm and was slowly dried on a tray at room temperature for 24 h. The dry granules were packed in a dose of 2000 mg in sealed closure bags.

| g. Gonadorelin nasal spray | |
| --- | --- |
| Gonadorelin | 1.0 mg |
| Benzyl alcohol | 20 mg |
| Acrylic acid/maleic acid copolymer | 75 mg |
| (50:50) sodium salt (molecular weight 50000) | |
| 1N HCl to pH 7.0 | |
| Water | ad 1000 mg |

700 g of purified, sterile water were mixed with 20 g of benzyl alcohol. Then 50 g of acrylic acid/maleic acid copolymer were dissolved therein and the pH was adjusted to 7.0 with 1N HCl while stirring. After addition of the gonadorelin, the mixture was stirred for 0.5 h, the remaining water was added until the weight was 1 000 g, the solution was sterilized by filtration through a 0.22 µm filter and was packed in nasal spray bottles.

| h. Ranitidine solution | |
| --- | --- |
| Ranitidine HCl | 20 mg |
| Acrylic acid/maleic acid copolymer | 100 mg |
| (50:50) sodium salt (molecular weight 50000) | |
| Sucrose | 50 mg |
| Benzalkonium chloride | 1 mg |
| 1N HCl | 54 mg |
| Purified water | 775 mg |
| Solution weight | 1000 mg |

20 g of ranitidine HCl, 50 g of sucrose and 1 g of benzalkonium chloride were dissolved in 775 g of purified water with stirring. After addition of 100 g of acrylic acid/maleic acid copolymer (50:50) sodium salt and 54 g of 1N hydrochloric acid, stirring was continued until everything had dissolved and the solution was filtered through a 5 µm filter and packed in 50 g bottles.

We claim:

1. A pharmaceutical composition for improving mucosal permeability, which comprises an active ingredient and an effective amount of a (meth)acrylic acid/maleic acid copolymer comprising
   a) 10–90 mol % of (meth)acrylic acid,
   b) 90–10 mol % of maleic acid and
   c) 0–40 mol % of hydroxyalkyl (meth)acrylate, alkyl (meth)acrylate or vinylsulfonic acid or a mixture thereof.

2. A method for improving mucosal permeability to pharmaceutically active ingredients, wherein a pharmaceutical composition comprising a pharmaceutically active ingredient and an effective amount of a (meth)acrylic acid/maleic acid copolymer comprising
   a) 10–90 mol % of (meth)acrylic acid,
   b) 90–10 mol % of maleic acid and
   c) 0–40 mol % of hydroxyalkyl (meth)acrylate, alkyl (meth)acrylate or vinylsulfonic acid or a mixture thereof, is administered to a host.

3. The method of claim 2, wherein the molar ratio of (meth)acrylic acid to maleic acid is from 70:30 to 30:70.

4. The pharmaceutical composition defined in claim 1, which is in the form of tablets, extrudates, granules, pellets, powders, capsules, suppositories, oinments, suspensions, solutions or emulsions.

5. The pharmaceutical composition defined in claim 1, which comprises at least 10% by weight of the (meth)acrylic acid/maleic acid copolymer.

6. The pharmaceutical composition defined in claim 1, wherein the copolymer is in the unneutralized, partially neutralized or neutralized form, and which composition may further comprise a base or a proton acceptor when the copolymer is in the unneutralized form.

7. The pharmaceutical composition defined in claim 1, wherein the active ingredient is wholly or partly in the form of a salt with the (meth)acrylic acid/maleic acid copolymer.

8. The method of claim 2, wherein the pharmaceutical composition is administered orally, sublingually, buccally, rectally, pulmonary or nasally or through the mucosa of the eye.

9. The pharmaceutical composition defined in claim 1, wherein the molar ratio of (meth)acrylic acid to maleic acid is from 70:30 to 30:70.

* * * * *

UNITED STATES PATENT AND TRADEMARK OFFICE
CERTIFICATE OF CORRECTION

PATENT NO.: 6,004,575

DATED: December 21, 1999

INVENTOR(S): LUESSEN et al.

It is certified that error appears in the above-identified patent and that said Letters Patent is hereby corrected as shown below:

Insert the following missing priority data on the cover page:

--[30]     Foreign Application Priority Data
Aug 1, 1996    [DE]    Germany    .................. 196 31 085.7--.

Signed and Sealed this

Nineteenth Day of September, 2000

Attest:

Q. TODD DICKINSON

*Attesting Officer*     *Director of Patents and Trademarks*